United States Patent
Stephenson

(10) Patent No.: US 8,370,171 B2
(45) Date of Patent: Feb. 5, 2013

(54) METHODS FOR PROVIDING AN EASILY COMPREHENDIBLE RISK RATING FOR PHARMACEUTICAL PRODUCTS

(75) Inventor: Hugo Stephenson, Princeton, NJ (US)

(73) Assignee: Quintiles Transnational Corp., Durham, NC (US)

( * ) Notice: Subject to any disclaimer, the term of this patent is extended or adjusted under 35 U.S.C. 154(b) by 1140 days.

(21) Appl. No.: 11/754,140

(22) Filed: May 25, 2007

(65) Prior Publication Data

US 2008/0005174 A1    Jan. 3, 2008

(51) Int. Cl.
 G06Q 10/00    (2012.01)
 G06Q 50/00    (2012.01)
(52) U.S. Cl. ................................. 705/2; 705/3
(58) Field of Classification Search .................. 705/2–3; 600/300
 See application file for complete search history.

(56) References Cited

U.S. PATENT DOCUMENTS

| | | | | |
|---|---|---|---|---|
| 2004/0117126 A1* | 6/2004 | Fetterman et al. | ............... | 702/19 |
| 2008/0004913 A1* | 1/2008 | Sayre | ............... | 705/3 |
| 2008/0091466 A1* | 4/2008 | Butler et al. | ............... | 705/2 |
| 2010/0138161 A1* | 6/2010 | Gogolak | ............... | 702/19 |

OTHER PUBLICATIONS

Pregnancy Drug Safety Categorization Regulation at 21 CFR 201.57(f)(6)—Pregnancy, pp. 24-25, Apr. 1, 2002 Edition.
US FDA-Approved Drug Prescribing Information for Celgene's Thalomid(R) (thalidomide) capsules, black box warnings on p. 1.
US FDA-Approved Drug Prescribing Information for Roche's Accutane(R) (isotretinoin) capsules, black box warning on p. 1.

* cited by examiner

*Primary Examiner* — Luke Gilligan
(74) *Attorney, Agent, or Firm* — William D. Hare; McNeely, Hare & War LLP

(57) ABSTRACT

The invention relates to a method for assigning a risk rating to a medical product. The method includes assessing one or more threats associated with the medical product; assessing the level of experience with the medical product; and assigning a risk rating for the medical product to provide an indication of risk associated with the medical product. The method may be implemented as a webpage. For example, a new contraceptive may be assigned a risk rating of yellow for the general treatment population. This risk rating allows consumers to make an informed choice between different products on the basis of benefit versus risk, and help patients decide what steps they may wish to take to minimize their risk if they choose to take the new drug.

27 Claims, 7 Drawing Sheets

METHODS FOR PROVIDING AN EASILY COMPREHENDIBLE RISK RATING FOR PHARMACEUTICAL PRODUCTS

TECHNICAL FIELD

The field of the invention generally relates to methods, software, systems, and webpages for providing consumers, physicians, regulators, and manufacturers with a risk rating for pharmaceutical products, biologics and medical devices.

BACKGROUND

Drugs are approved by the US Food and Drug Administration (FDA) after undergoing clinical studies to show safety and effectiveness. The clinical studies involve phase I studies on a small population, approximately thirty patients, to demonstrate safety. Next the drug is put through phase II studies to determine dosing levels. These studies are on a larger population of approximately 100 to 300 patients. With the dosing levels established, the drug is studied on a significantly larger population of 3000 to 5000 patients to show effectiveness and look for indications that there may be safety concerns with the drug. After the drug is approved, the FDA may require post-approval, or phase IV, studies to obtain a more complete safety profile of the drug.

The safety and effectiveness information gathered from the clinical studies conducted to obtain approval are used to create the label. This information in the label, however, is not readily comprehendible by most patients, may be overwhelming, and is unlikely to inform the patient as to how the label applies to them as an individual. For example, the adverse events that a person would read in a typical drug label range from death to dizziness. Such a broad range of adverse events does not adequately inform a person of which adverse events apply to them.

Some US FDA-approved labels have a type of warning known in the industry as a black box warning. Examples of such drugs with black box warnings are Accutane®, the various generic versions of isotretinoin, and thalidomide. The black box warning is prominently displayed at the front of the FDA-approved labeling and is in the form of a black box surrounding text. In the Accutane® black box warning, the text describes precautions that should be taken when prescribed the drug, warnings about the drug and its potential adverse effects, special prescribing information and contraindications for the drug. The Accutane and isotretinoin black box warnings are directed to the threat of birth defects if women take the drug while pregnant. It should be noted that other threats are alleged to be associated with isotretinoin, including suicide, but only the threat of birth defects is included in the black box warning. It should be recognized that the black box warning is at most a binary indicator of a threat associated with the drug: its presence indicates the existence of the warning and its absence indicates only that a black box warning has not yet been required for the drug.

While a label informs the patient about the information known about the drug at one particular time, the label does not inform the patient about what is not yet known about the drug. It is not uncommon for the safety profile of pharmaceuticals to more completely emerge only after millions of patients have used the drug. The information that contributes to that safety profile typically emerges in a piece-meal fashion with sporadic adverse events reported and occasional studies published. For example, two drugs with similar labels for the same indication may nonetheless have different levels of risk that cannot be determined by a patient from reading the label because one drug has been used by millions more patients than the other drug and therefore its safety profile is more clearly known. Addressing in part the different levels of risk associated with newly approved drug, in the United Kingdom newly approved drugs have a symbol on their label to indicate that it is a newly approved drug.

Information that relates to a pharmaceutical's safety profile may be gathered from drugs in that class rather than the drug itself. For example, safety information relating to pharmaceuticals such as Baycol, a statin, and Vioxx, a COXII inhibitor, had implications for other pharmaceuticals in both classes. With respect to Vioxx, this information was not generally known to the patient community as the information developed, but only upon an announcement by the company after a large quantity of data had been gathered. The inventor has developed a system to keep consumers of pharmaceuticals more fully informed in a real-time manner about the risk associated with the pharmaceuticals that they are prescribed. Advantageously, the inventor has developed systems to provide a risk rating in a manner that is easily comprehendible.

Similar concerns exist for biologics and medical devices. For example, drug coated stents have been the subject of safety questions as a result of clinical reports. In the past the Dalcon Shield and silicone breast implants were the subject of safety concerns. Thus, there exists a similar need to inform consumers in a readily comprehendible manner about risk relating to the medical devices and biologics they may be using.

SUMMARY

In one general aspect, a method for assigning a risk rating to a medical product, the method includes:

assessing one or more threats associated with the medical product;

assessing the level of experience with the medical product; and assigning a risk rating for the medical product to provide an indication of risk associated with the medical product.

Embodiments of the method may include one or more of the following features. For example, the medical product may include one or more of a pharmaceutical product, a biologic product, and a medical device.

Assessing one or more threats may include assessing the severity of the threat. Assessing the severity of the threat may include one or more of a risk of permanent disability, death, and serious adverse event. Assessing one or more threats may include assessing the probability of the threat occurring.

Assessing one or more threats may include assessing the potential population affected by the threat. Assessing the potential population affected by the threat may include assessing a percentage of the population to which the threat applies.

Assessing the one or more threats comprises one or more of determining the population to which the threat applies, determining whether the population at risk as a result of the threat can be identified in advance, and determining an indicator of usage of a second medical product for which there is an interaction with the first medical product.

The method may further include pooling the assessment of each threat. The method may further include assigning an indication of a level of experience with the medical product. The method may further include determining whether the medical product is an orphan product.

The risk rating may be implemented as a gradated rating having more than two grades. The risk rating may be implemented with at least three grades. The three grades may be in the form of three symbols.

The method may assess more than one threat. Assigning a risk rating may further include providing guidance associated with the risk rating. The method for assigning a risk rating to a medical product may be implemented on a webpage.

In another general aspect, there is provided a webpage for providing a risk rating for a medical product. The webpage may be configured to receive input relating to a drug; and display a risk rating for the drug. The webpage includes instructions for assessing one or more threats associated with the medical product, assessing the level of experience with the medical product, and assigning a risk rating for the medical product to provide an indication of risk associated with the medical product.

Embodiments of the webpage may include one or more of the following features. For example, the medical product may be one or more of a pharmaceutical product, a biologic product, and a medical device.

Assessing the one or more threats may include assessing the severity of the threat. Assessing the severity of the threat may include one or more of a risk of permanent disability, death, and serious adverse event.

Assessing one or more threats may include assessing the probability of the threat occurring. Assessing one or more threats may include assessing the potential population affected by the threat.

The risk rating may be implemented as a gradated rating having more than two grades. The risk rating may be implemented with at least three grades. The three grades may be in the form of three symbols. The webpage may assess more than one threat. Assigning a risk rating may further include providing guidance associated with the risk rating.

The details of various embodiments of the invention are set forth in the accompanying drawings and the description below. Other features and advantages of the invention will be apparent from the description, the drawings, and the claims.

DETAILED DESCRIPTION

Figure 1:
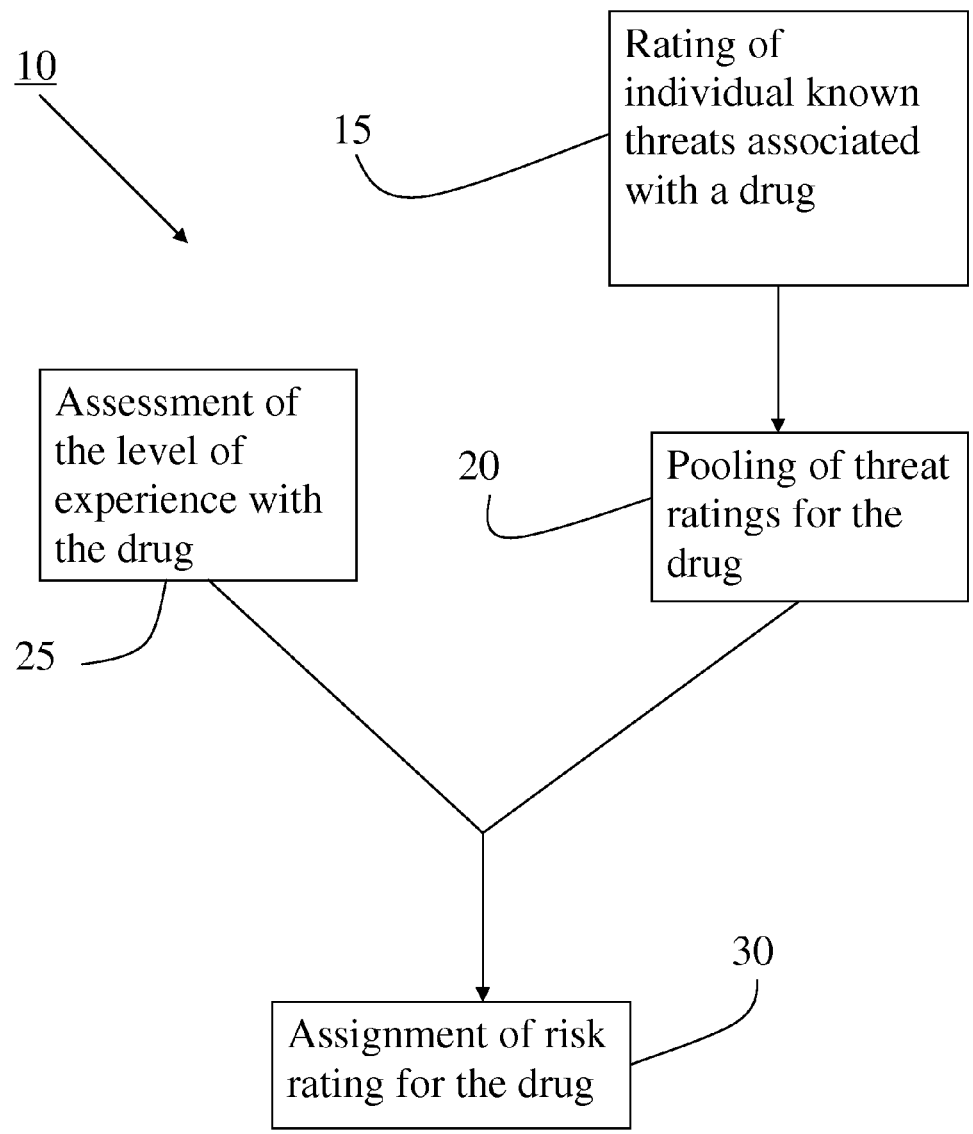
FIG. 1 is a flowchart for an algorithm to establish a risk rating for a drug based on the threats associated with the drug and the level of experience with the drug.

The inventor has developed systems for providing real-time risk ratings, or safety profile indicators, about medical products, such as pharmaceuticals. The systems provide a risk rating for the pharmaceutical in a manner that is easily comprehendible to consumers, physicians, regulators, and manufacturers. In one aspect, the risk rating is gradated to distinguish between different levels of risk associated with a drug. This is in contrast to the black box warning described above which is not gradated but instead is binary: present or absent. In another aspect, the risk rating is based on pooling multiple threats rather than a single threat. Again, this is in contrast to the black box warning described above which considers a single threat—birth defects associated with taking the drug while pregnant.

Although equally applicable to medical devices and biologics, for ease of explanation the system is described only with respect to pharmaceuticals. As described in greater detail below, on a most basic level, the system uses an algorithm to rate individual, known threats to safety associated with a drug, pool these individual threat levels, assess the level of experience that exists for the drug, and assign a risk rating for the drug. In this process, the systems assess a drug based on what is known and not known about the drug, and provide a meaningful categorization of risk. The system can be applied to the general population to assign a general risk rating, or to a sub-population in order to assign a personalized risk rating for an individual.

As a benefit to patients, the risk ratings are configured to be easily comprehendible and may be visually-based (e.g., letter, word, color, number(s), shape, etc.). The systems optionally provide guidance for patients and physicians regarding additional actions that may need to be taken. The ratings are determined as a function of at least one or more of the following factors: the probability of different threats occurring, their potential severity, the proportion of people potentially affected by the threats, and the level of experience available for the drug. Other factors may be included in the function as needed to improve any aspect of the risk rating.

The following terms used in the application are defined as follows. A threat is an individual item of safety information that exists for a drug and can be derived from one or more sources, e.g., the labeling, a clinical study reported in a journal article, an FDA alert on the drug or even class of drugs of which the subject drug is a member, a news article, an anecdotal report in a blog, etc. Moreover, there may be multiple threats contained within a single source of information. For example, a particular drug's label may have warnings, precautions, contraindications, adverse reactions, drug-drug interactions, and other threats. Within the warnings in the labeling there may be separate warnings relating to a number of factors, such as liver function, affect on blood pressure, etc. Each of these individual factors is considered a threat. Similarly, if a journal article reports on a large scale post-marketing clinical study of a drug, the article may report that certain subpopulations were the subject of a particular safety concern. Each of these individual safety concerns is considered a threat. Other subpopulations within the study may have had drug-drug interactions. Again, each of these drug-drug interactions is considered a threat.

FIG. 1 is a flowchart for an algorithm 10 to calculate a risk rating for a drug. The algorithm 10 includes an assessment of individual known threats associated with a drug to rate each individual threat (step 15). In assessing the individual threats associated with a drug, the algorithm takes into account factors such as (a) absolute and/or relative size of the population that will be affected by the threat; (b) severity of the outcome if the threat should occur; and (c) probability of the threat occurring. These are but some factors that can be included in assessing the threats and not all of the factors must be used.

The assessment of the factors can be performed using different weightings. In particular, the weighting of the factors can be adjusted on a subjective basis depending upon the emphasis intended in setting up the algorithm 10. For example, in one possible implementation, more weight can be put on the severity of the outcome than on the size of the population or the probability of the threat occurring.

After rating the individual, known threats (step 15), the algorithm then pools the ratings of the threats existing for the drug (step 20). The pooling can be configured in a number of manners. In one basic implementation, if the ratings are based on a numerical ordering the pooling can be configured to sum the assigned values and divide by the number of values. As one example, the algorithm can be used to evaluate only the probability of an occurrence. In that algorithm a low probability may be assigned a rating value of one, a medium risk may be assigned a rating value of two and a high risk may be assigned a rating value of three. In that scenario there are a total of twelve threats broken down into three threats of value one, four threats of value two and five threats of value three, and the pooling would give a rating value of 2.167 for the drug, which is between a medium and a high probability. In this implementation, the pooling is based on the assumption that a probability level for a drug is based on an average of the probability levels determined for the individual threats. In another implementation using the same rating values for the individual probability levels, the output may be configured to be more cautious. In such an implementation, the output may be determined based on the assumption that the probability level should be set at the highest level that includes at least a certain percentage, e.g., 25%, of the probability levels determined for individual threats. Using the above data, where five of twelve (i.e., 42%) of the probabilities are high probability, the probability level pooling gives a rating value of high probability for the drug. If a total of three out of twelve, (i.e., 25%) of the individual probability levels determined were a combination of medium and high level, the probability level pooling would give a medium level of probability for the drug.

In yet another implementation, based on extreme caution, the pooling would be configured to give a rating corresponding to the highest level of probability that any one threat exhibits. Thus if eleven of the twelve are low probability but one of the twelve is a high probability, in this model of extreme caution the pooling would give a rating value corresponding to a high level of probability to the drug.

It should be understood that level of probability of a threat occurring is but one factor that could be used in rating the threats and other factors could be used in the pooling step. For example, in yet another implementation, a severity rating used with the individual, known threat may be in the form of a letter, e.g., D for the highest level of severity, C with a lesser level of severity, B with an even less level of severity, and A with the least level of severity. In pooling the individual threats, the letter rating for severity could be used with another output from the pooling step. Thus, if the probability level pooled is a percentage (i.e., ranging between 0% to 100%), a particular pooling may give a value of D75 to indicate a threat with the highest level of severity and a 75% probability.

The algorithm 10 also can use an assessment of the level of experience with a drug (step 25) in calculating a risk rating for the drug (step 30). Experience can be measured in a number of manners, such as years on the market, number of prescriptions, number of patients studied during the clinical trials, number of patients taking the drug, number of countries in which the drug has been approved and marketed, etc. These factors relating to experience are designed to capture the safety knowledge that is gained through use of the drug as well as have an effect on the assessment if there is relatively little experience with the drug.

The algorithm 10 then assigns a risk rating for the drug (step 30) based on a combination of the pooling of threat ratings for the drug (step 20) and assessment of the level of experience with the drug (step 25). In one implementation of the risk rating step, the resulting risk rating of the algorithm 10 is defined according to the system illustrated in Table 1.

TABLE 1

Risk Rating

| Risk Rating | Risk Level | Patient Advisory |
|---|---|---|
| RED | HIGH | Should only be used under strict supervision |
| ORANGE | ELEVATED | Use within a customized risk management plan |
| YELLOW | GUARDED | Be on the lookout for safety events |
| BLUE | GENERAL | Use under the normal care of a physician |
| GREEN | LOW | Suitable for widespread use |

Figure 2:
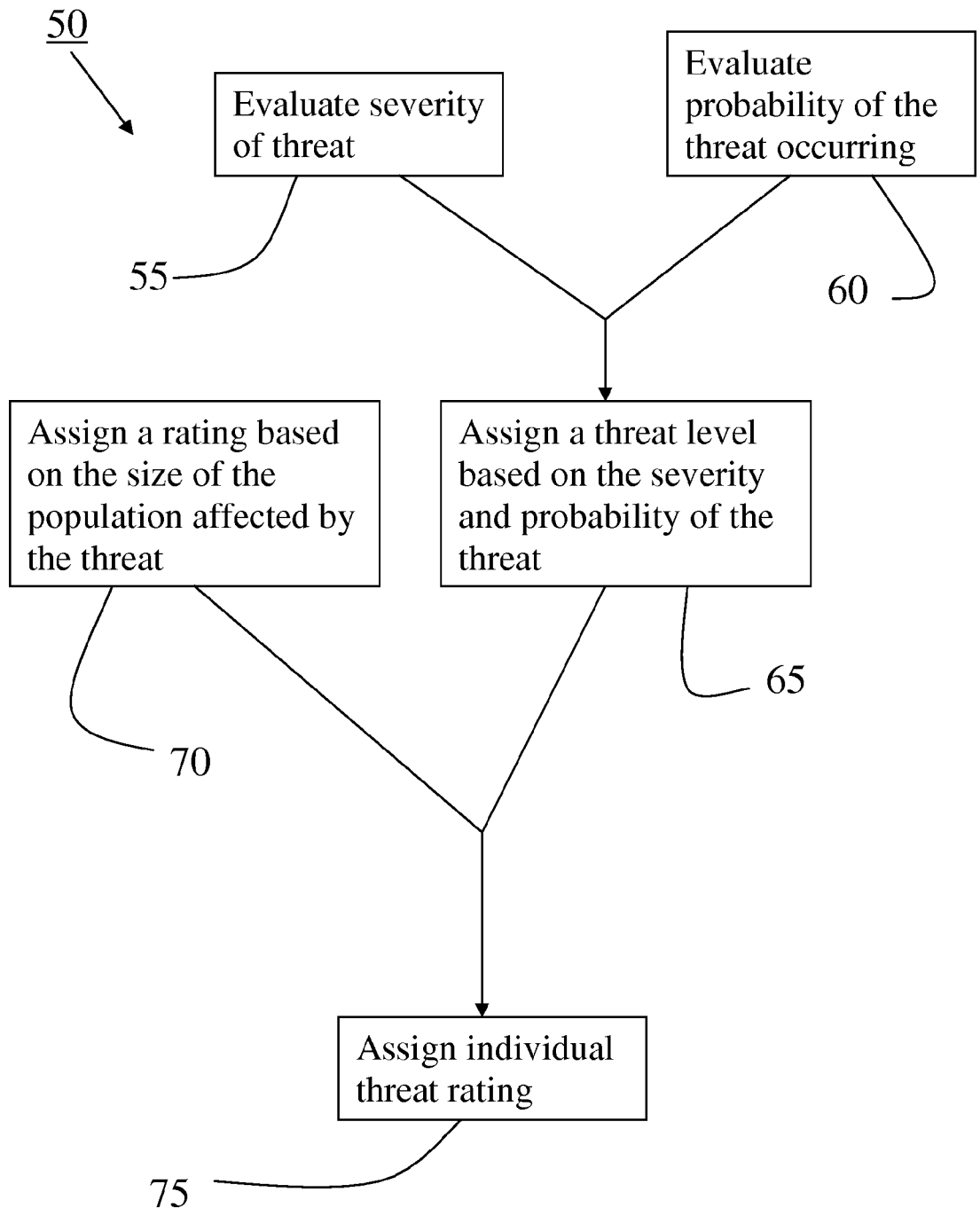
FIG. 2 is an implementation of step 15 of the flowchart of FIG. 1 for rating the individual threats known to be associated with a drug.

FIG. 2 provides a more detailed explanation of the rating step 15 of FIG. 1, implemented as an algorithm 50. Initially the algorithm 50 is used to evaluate the severity of a threat (step 55). Factors that may be used to evaluate severity of the threat include the outcome expected if the threat occurs. The expected outcome may be found in the labeling, from the source of the threat (e.g., described in the journal article that reported the threat), or based on a medical judgment. Examples of outcomes include permanent disability, death, and serious adverse effect. Other factors used in evaluating severity include whether the risk level of the outcome is high, elevated, or a general warning. Consequently, the result of the evaluation of step 55 will be either a description of the outcome, e.g., permanent disability, or an indicator of the outcome, e.g., a numerical value of 1 for death, a numerical value of 2 for permanent disability, etc.

The algorithm 50 also evaluates the probability of the threat occurring (step 60). This evaluation can be a specific probability (1 in 10,000) or a probability range (between 1 in 10,000 and 1 in 20,000, etc.). The probability value can be based on a number of methods, such as reviewing historical data (e.g., the clinical studies used to obtain FDA approval), epidemiological studies, or a medical judgment. The result of step 60 can be in the form of a probability or an indicator of probability. One example of an indicator of probability is the use of terms such as high, elevated, and low.

Next, the algorithm 50 assigns a threat level (step 65) that is based on both the severity of the threat (step 55) and the probability of the threat (step 60). The threat level can be based on equal weights for the severity of the threat and the probability of the threat occurring. Such an equal weighting, however, is not necessary and can be in a range that varies from being based entirely on one of the two factors to the other of the two factors. Moreover, the threat level can be based on other, different weightings of each factor. This assignment of a threat level is described in more detail below.

Along with assigning a threat level (step 65), the algorithm also assigns a penetration rating based on the size of the population affected by the threat (step 70). This assignment of a penetration rating is described in more detail below.

The algorithm 50 next assigns a threat rating for each particular threat being evaluated (step 75). The individual threat rating calculated or otherwise determined will be a combination of the inputs from steps 65 and 70. The threat rating assigned may be in the form of an indicator, the form of the indicator being varied. For example, the indicator may be a color, shape, number, text, code, etc. For example, in one implementation, the indicator may merely be the merging of the penetration rating (step 70) and the threat level (step 65). Thus, if the penetration rating is 85% and the threat level is a letter C, the indicator resulting from step 75 may be in the form of an 85 C. Alternatively, the penetration and risk levels can be assigned numbers that can be combined in some manner to imply the individual threat rating. Thus, if the maximum penetration rating that can occur is given a value of 50 and the highest threat level that can be assigned is a value of 50, then the highest individual threat rating possible is a 100 if the two values are added, or a 50 if the two values are averaged.

The penetration rating of step 70 of the algorithm 50 illustrated in FIG. 2 can be implemented using a variety of factors to assign a penetration rating for a particular threat. For example, in one implementation of this portion of the algorithm, the penetration rating may be assigned as illustrated in Table II, below.

TABLE II

Categorization of Level of Penetration of Population Affected by a Threat

| Penetration Rating | Factors |
|---|---|
| 85 | If the threat applies to a sub-population > 85% of the treatment population<br>If population at risk cannot be identified in advance<br>If the threat involves an interacting drug with an OTC drug |
| 15 | If the threat applies to a sub-population > 15% treatment population<br>If the threat involves an interacting drug that is a high volume prescription drug in the treatment population |
| 1 | If the threat applies to a sub-population > 1% treatment population<br>If the threat involves an interacting drug that is a non-high volume, non-specialist drug in the treatment population |
| 0 | If the threat applies to a sub-population < 1% treatment population<br>If the threat involves an interacting drug that is a specialist only drug in the treatment population |

These are exemplary of the categorizations of the penetration and the factors that can be used to determine the population potentially or actually affected. The factors in Table 2 relate to three factors: the amount of a sub-population to which the threat applies, whether the population at risk can be identified in advance, and the nature of an interacting drug if the threat involves a drug-drug interaction. As can be expected, these factors and categorizations can be modified and/or replaced depending upon the design of the assessment and algorithm.

Figure 3:
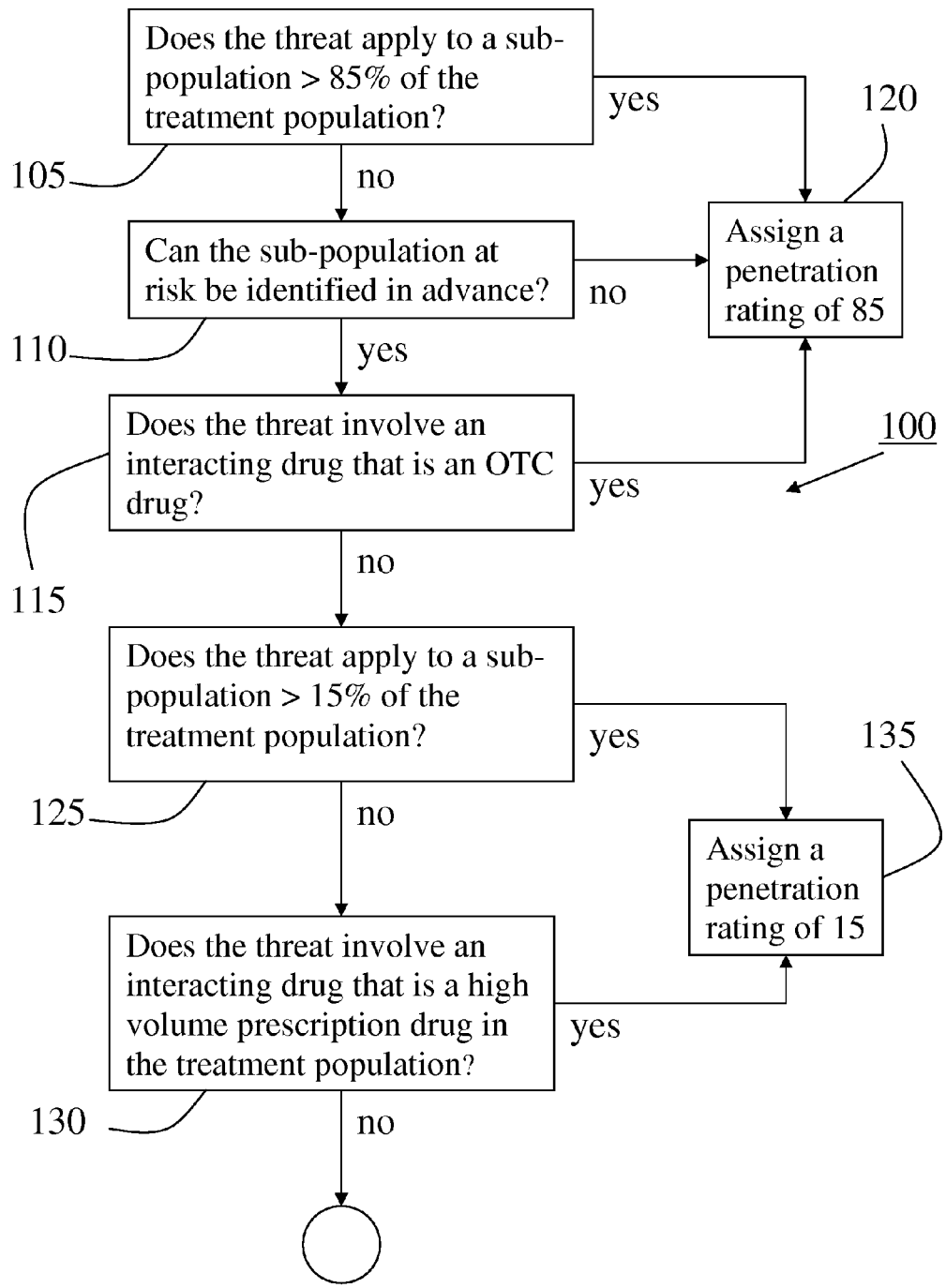
FIG. 3 is an implementation of the flowchart of FIG. 2 for an algorithm for assigning penetration ratings for individual threats.
Figure 3:
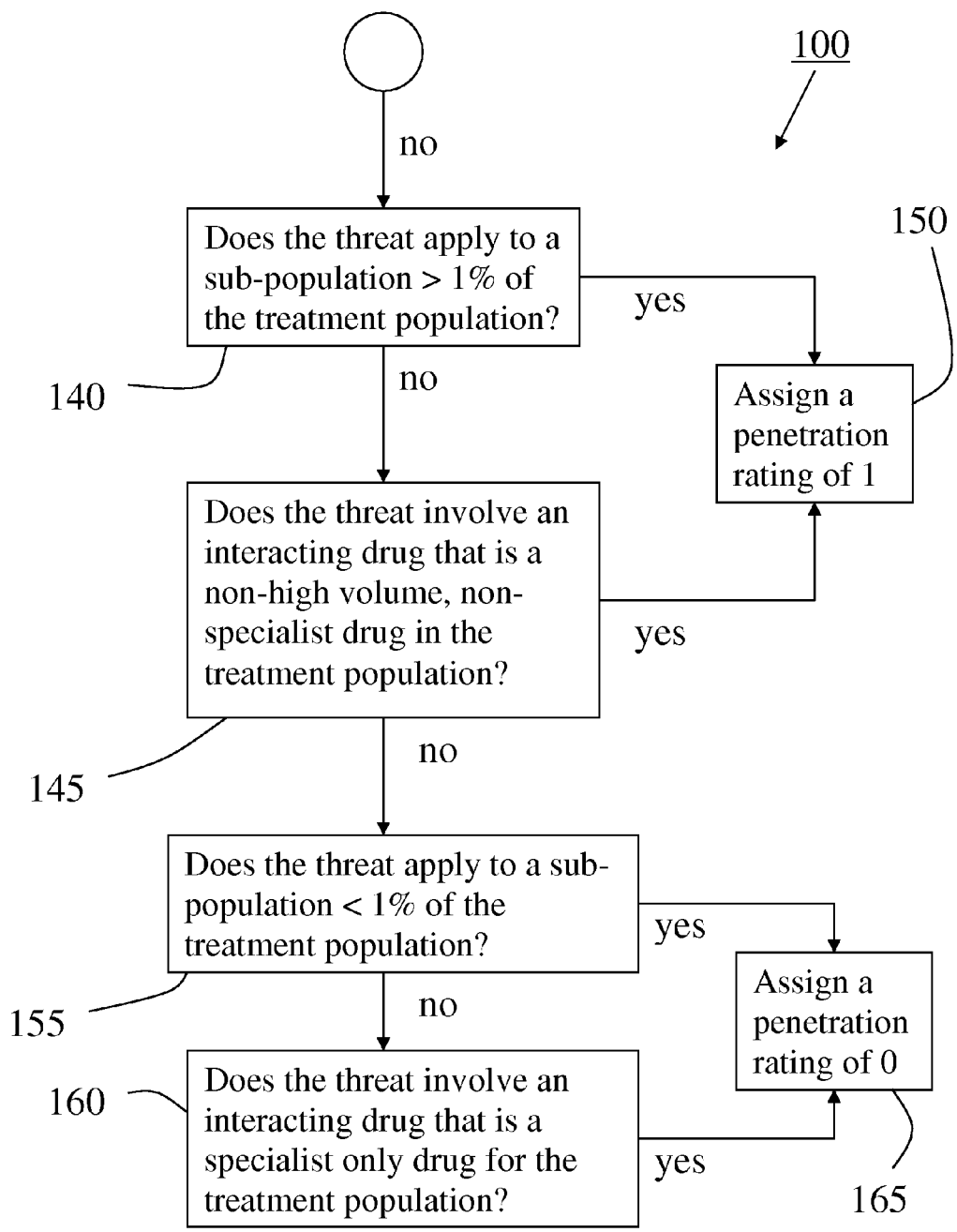

In the flowchart illustrated in FIG. 3, a penetration algorithm 100 determines the extent to which a threat applies to a population of patients. Applying the penetration algorithm 100 illustrated in FIG. 3 to a particular threat results in the threat being categorized as having one of four penetration ratings: 85, 15, 1 or 0. It should be noted that the penetration of a particular threat within a specific population can be rated in numerous manners. The penetration can be divided, for example into four groups: MOST, MANY, SOME, or FEW; or divided into two groups: most and few, or more than half and less than half. The penetration rating also can be made up of narrower ranges or greater divisions: less than one third of the patients, greater than one third of the patients but less than two thirds of the patients, and greater than one third of the patients but less than all of the patients. The intent is to apply the algorithm 100, at least in part, based on the number of patients potentially or actually subject to the threat.

Initially, the penetration rating algorithm 100 examines whether the threat applies to a particular proportion of the treatment portion (step 105). In the implementation illustrated in FIG. 3, the algorithm is set to determine whether the threat applies to a sub-population that is greater than 85% of the treatment population. If the threat applies to a sub-population that is greater than 85% of the treatment population, then the algorithm assigns a penetration rating to the threat of 85 (step 120). If the condition is not true, the algorithm determines whether the population at risk can be identified in advance. If the population cannot be identified in advance, then the algorithm assigns a penetration rating to the threat of 85 (step 120). One rationale for equating the same penetration rating for 85% of the population and not being able to identify the population in advance is that one should set the penetration rating at a high level when the population at risk cannot be identified in advance.

If the population can be identified in advance, the algorithm determines whether the threat involves an interacting drug that is an over-the-counter (OTC) drug (step 115). An OTC drug can be purchased without a doctor's prescription and thus without a doctor or pharmacist's intervention to warn the patient about potential interactions. Thus, the penetration rating is given the highest penetration rating possible, namely, 85 (step 120) in this algorithm. Of course, any other indicator of penetration may be used, such as the absolute number of prescriptions written for the interacting drug, prescriptions written on an annual basis for the interacting drug, the number of prescriptions written for the entire class of drugs in which the interacting drug is a member, or a basis that provides a means to differentiate between levels of prescriptions written for a drug or class of drugs.

It should be noted that steps 105, 110, and 115 are arranged in one particular order. This arrangement, however, is not to be construed as limiting the method to this particular order. In fact, the order of these three steps can be reversed or re-ordered and give the same result when applied to the same set of conditions.

If the threat does not involve a factor that causes the algorithm to assign a penetration rating of 85, the algorithm 100 next determines whether the threat should be assigned a penetration rating of 15 (steps 125, 130, 135). The algorithm determines whether the threat applies to a sub-population that is greater than fifteen percent of the treatment population (step 125) or involves an interacting drug that is a high volume prescription drug (step 130). If either of these conditions is true, the algorithm assigns a penetration rating of 15 (step 135). While a high volume prescription drug is highly prescribed, it nonetheless is subject to a doctor or pharmacist's review before being taken by a patient. Thus, a physician and/or pharmacist will be aware of, or can inquire about, the other drugs being taken by the patient. This will reduce the population that takes the interacting drug along with the drug that is the subject of the threat and for which the algorithm 100 is being processed. Although steps 125 and 130 result in the same penetration ratings, the algorithm 100 can be configured to assign different penetration ratings to each step.

If the threat does not involve a factor that causes the algorithm to assign a penetration rating of 15 in steps 125 or 130, the algorithm 100 next determines whether the threat should be assigned a penetration rating of 1 (steps 140, 145, 150). The algorithm determines whether the threat applies to a sub-population that is greater than one percent of the treatment population (step 140) or involves an interacting drug that is a non-high volume prescription drug (step 145). If either of these conditions is true, the algorithm assigns a penetration rating of 1 (step 150). Similar to steps 125 and 130, the algorithm 100 can be modified to assign different penetration rating to steps 140 and 145.

If the threat does not involve a factor that causes the algorithm to assign a penetration rating of 1, the algorithm 100 next determines whether the threat should be assigned a penetration rating of 0 (steps 155, 160, 165). The algorithm determines whether the alert applies to a sub-population that is less than one percent of the treatment population (step 155) or involves an interacting drug that only a specialist will prescribe (step 160). If either of these conditions is true, the algorithm assigns a penetration rating of 1 (step 165).

Figure 4:
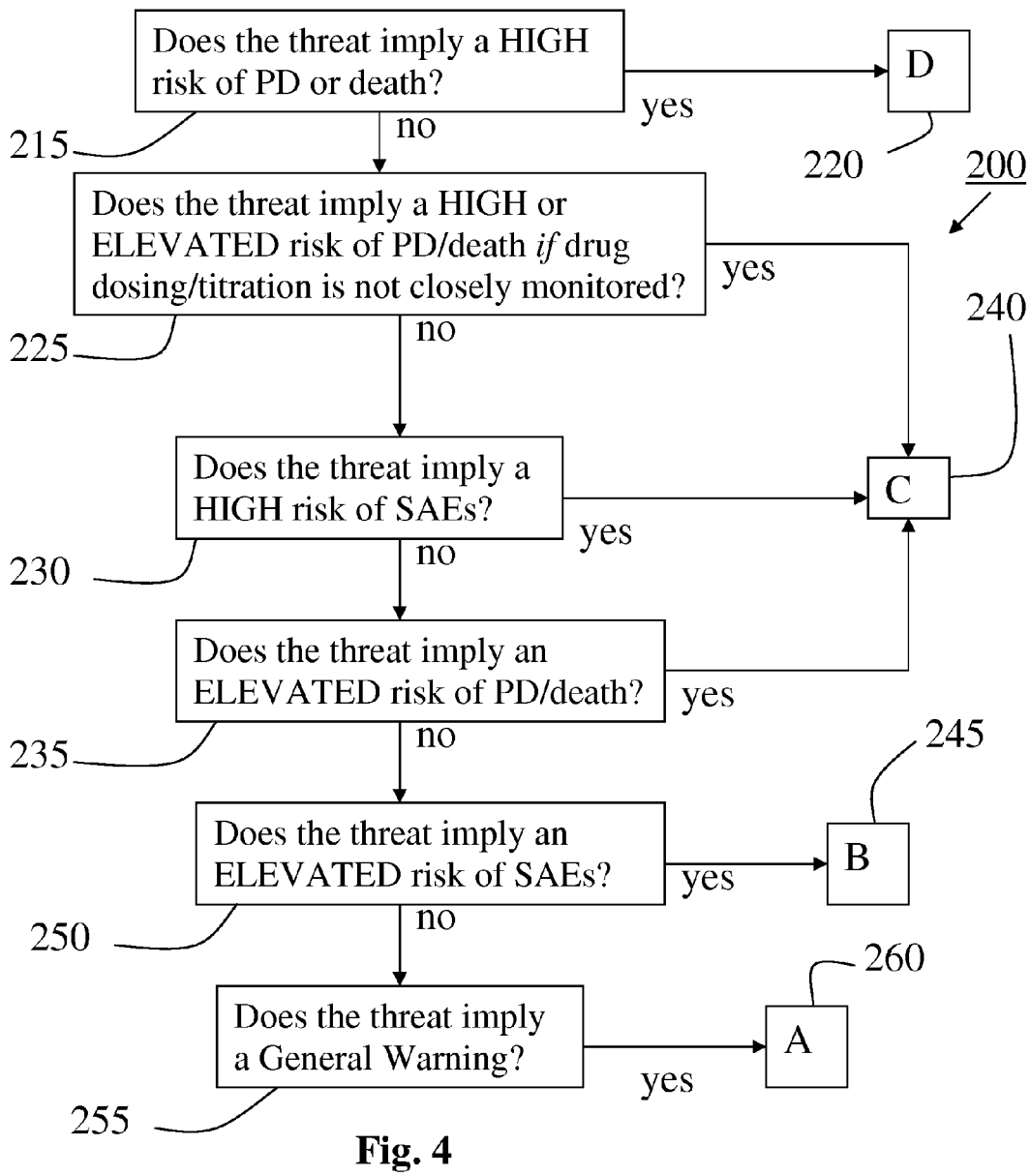
FIG. 4 is an implementation of the flowchart of FIG. 2 for an algorithm for assigning threat levels for individual threats.

Referring to FIG. 4, an algorithm 200 implements step 65 of the algorithm 50 (FIG. 2) to calculate a threat level as an indicator of risk. In the implementation illustrated in FIG. 4, the threat level assigned is based on the letters A, B, C and D, although other indicators of risk, such as a color coded system, can be used instead. Table III is a table showing the implementation used in FIG. 4 to assess the risk of the threat and assign an indicator of risk for each threat. Table III also provides examples of the threats that correspond to the risk level and indicator of risk. For the purposes of Table III, the terms HIGH RISK and ELEVATED RISK are defined as follows: (a) HIGH RISK: a likelihood of permanent disability (PD) or death of 1/10,000 or other serious adverse effect (SAE) of 1/1,000; and (b) ELEVATED RISK: a likelihood of PD or death of 1/100,000 or other SAE of 1/10,000. The output of the safety algorithm is the assignment of threat level.

TABLE III

Threat Level Indicator

| Risk Level | Threat Level | Examples of Threat |
|---|---|---|
| HIGH risk of PD/death | D | Absolute contraindications, CLASS 1 (ORCA) DDIs, black box warnings |
| HIGH or ELEVATED risk of PD/death if drug dosing/titration not closely monitored | C | e.g. insulin, erythropoetin, warfarin |
| HIGH risk of SAEs | C | Relative contraindications, warnings |
| ELEVATED risk of PD/death | C | Precautions |
| ELEVATED risk of SAEs | B | Precautions |
| General warning | A | General label change |

To implement the safety algorithm 200, the algorithm initially determines whether the threat implies a high risk of permanent disability ("PD") or death (step 215). As noted above, a high risk of permanent disability or death is defined in terms of probability of the event associated with the threat occurring or any other serious adverse effect occurring. If the threat implies a high risk of permanent disability or death, the algorithm assigns a threat level of D (step 220).

If the threat does not imply a high risk of permanent disability of death, the algorithm 200 will determine whether the threat involves a HIGH or ELEVATED risk of permanent disability or death if the drug dosing or titration is not closely monitored (step 225). Examples of drugs for which this condition may be true include insulin, erythropoetin, and warfarin. If the condition is true, the algorithm assigns a threat level of C (step 240). If the condition is not true, the algorithm determines whether the threat implies a HIGH risk of serious adverse events occurring (step 230). Again, the definition for HIGH risk described above is used in determining the level of risk. If the condition is true, the algorithm assigns a threat level of C (step 240). If the condition is not true, the algorithm 200 determines whether the threat implies an ELEVATED risk of permanent disability or death (step 235). The definitions of risk described above are used to determine the level of risk, i.e., HIGH or ELEVATED, involved with the threat. If the condition is true, the algorithm assigns a threat level of C (step 240).

If the condition is not true, the algorithm 200 determines whether the threat implies an ELEVATED risk of serious adverse events (step 250). If the condition is true, the algorithm assigns a threat level of B (step 245). If the condition is not true, the algorithm 200 assigns a threat level of A (step 260). Thus, after the application of the algorithm 200 to a particular threat, the algorithm has assigned a threat level of either A, B, C or D for that threat.

Figure 5:
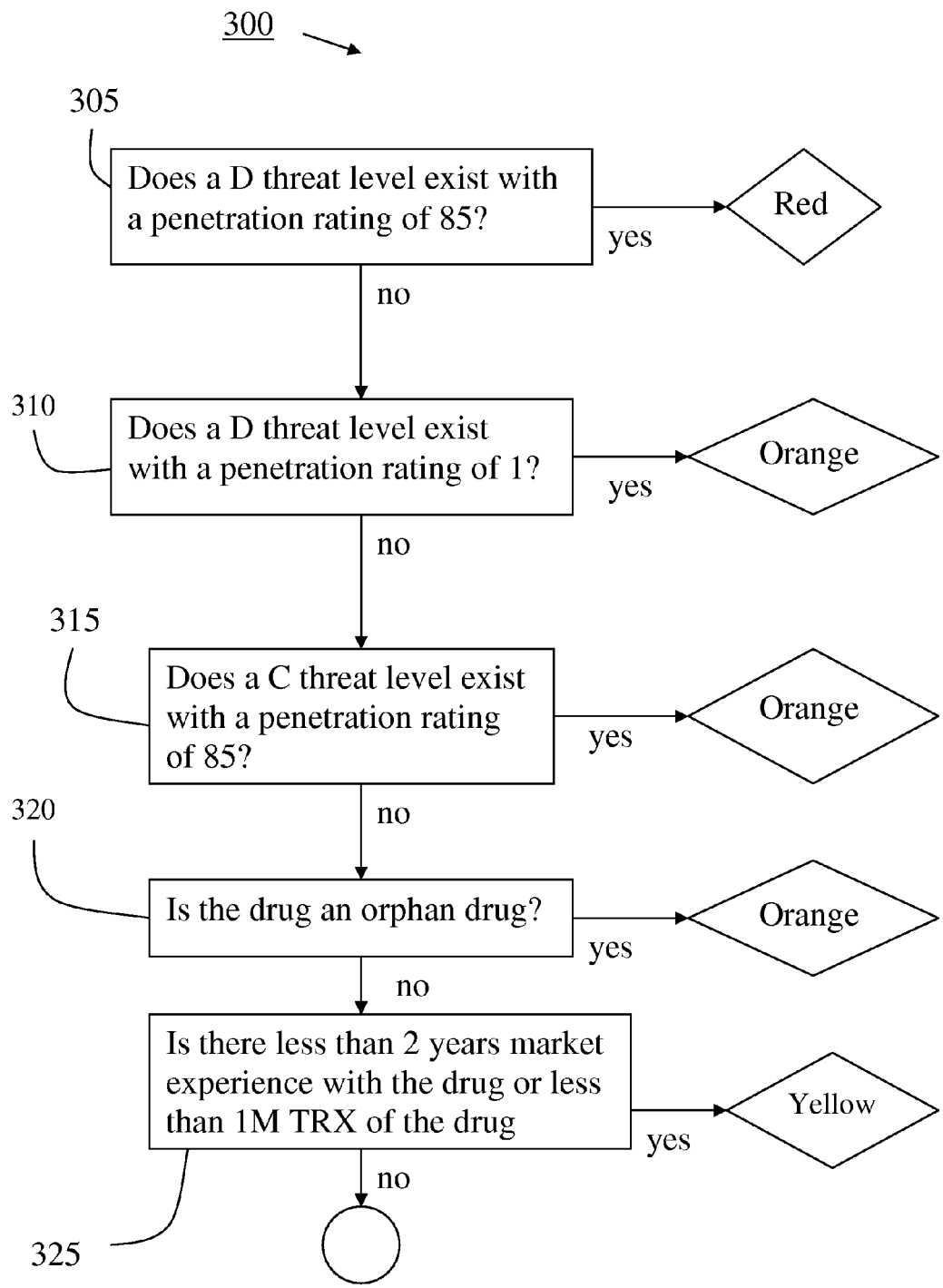
FIG. 5 is an implementation of the flow chart of FIG. 1 for an algorithm for assigning a risk rating for a drug given previously assigned threat levels and penetration ratings for different known threats, and the level of experience that exists for the drug.
Figure 5:
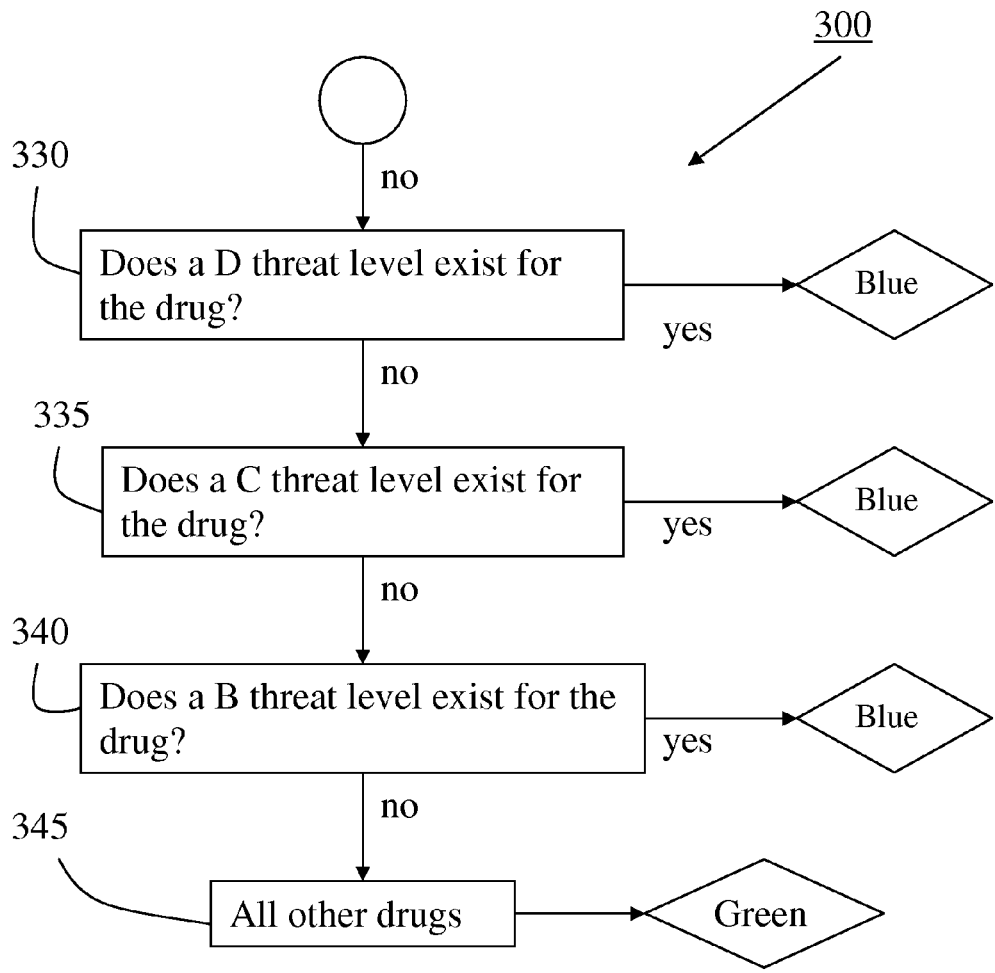

Referring to FIG. 5, a risk rating assignment algorithm 300 assigns a risk rating to indicate the level of risk for a pharmaceutical based on the output of the algorithms 100 and 200 illustrated in FIGS. 3 and 4, respectively, and the level of experience available for the drug. The algorithm 300 loosely corresponds to step 30 of FIG. 1, in which the algorithm 10 assigns a risk rating for a drug. The algorithm 300 is arranged to sort the risk associated with the drug in decreasing levels of risk. Referring to the conditional questions of step 305, the algorithm determines whether a threat with a high threat level and penetration rating exists for the pharmaceutical. In step 305 of the algorithm, if a threat with a D threat level risk and penetration rating of 85 exists, (from FIGS. 3 and 4, algorithms 100 and 200, respectively), the algorithm 300 assigns a red risk advisory rating to the pharmaceutical overall. In FIGS. 3 and 4, the penetration and threat level is assessed for each threat. In FIG. 5, the algorithm 300 considers all of the assessments of the individual threats determined in FIGS. 3 and 4 to assign a risk rating to the drug overall.

If the condition of step 305 is not true, then the algorithm 300 determines the conditions set forth in step 310: does a threat with a D threat level exist with a penetration rating of 1? As in step 305, the input for assessing the condition of step 310 is the output of the algorithms 100 and 200 of FIGS. 3 and 4, respectively. If this condition is true, the algorithm assigns an orange risk rating to the pharmaceutical. If the condition is not true, the algorithm determines the condition of step 315: does a threat with a C threat level exist with a penetration rating of 85 patients. If the condition of step 315 is true and a threat with a C threat level exists with a penetration rating of 85, the algorithm assigns an orange risk rating to the pharmaceutical.

If the condition of step 315 is not true, the algorithm 300 determines the condition of step 320: is the drug an orphan drug. As illustrated in FIG. 5, if the drug is an orphan drug, the drug is assigned an orange risk rating. One rationale for assigning an orange risk rating to an orphan drug is the relatively small number of people in whom the drug has tested and used.

If the drug is not an orphan drug (i.e., the condition of step 320 is not true), the algorithm determines the condition of step 325: is there less than two years of market experience with the drug or have there been less than one million prescriptions written for the drug. If the condition is true (i.e., less than two years on the market or less than one million prescriptions), the drug is assigned a yellow risk rating. This condition is based on the understanding that the safety profile of a drug may be known more completely only after being marketed for a length of time or after a certain number of people have been prescribed the drug. The values of two years and one million prescriptions can be modified based on the knowledge gained through experience. For example, if FDA were to increase the number of years a drug must be tested, or the number of patients required in the phase III clinical studies, prior to approval, those both could have an impact on the condition set in step 325 because they both would be expected to provide more safety profile information before approval. Obtaining more safety information prior to approval and marketing is expected to change the condition of step 325 by reducing the number of years on the market and the number of prescriptions written. Of course, if public pressure demands faster approval of drugs with less regulatory oversight, it would be expected that both conditions of step 325 would be increased.

It should be noted that in contrast to the assessments made at steps 305, 310, and 315, the assessments made at steps 320 and 325 are not based on inputs from the algorithms 100 and 200 of FIGS. 3 and 4, respectively. Instead, this is input derived from other sources. For example, FDA designates certain drugs with the orphan designation based on the size of the population that will be prescribed the drug. The number of years of market experience can be obtained from a number of sources, such as the FDA's web page listing of approvals of drugs, which includes the date of approval. The number of years of market experience and the number of prescriptions written both can be obtained from information providers such as IMS Health.

If the condition of step 325 is not met, then the algorithm will determine the condition of step 330: does a threat exist with a D threat level for the drug? As will be obvious by examining the flow of algorithm 300, the algorithm will have already determined whether a D threat level exists for a penetration value of both 85 and 1. Thus, step 330 effectively determines whether a D threat level exists for the drug for a penetration value of 0 or greater. If the condition of step 330 is met, the algorithm assigns a risk rating of blue to the pharmaceutical.

If the condition of step 330 is not met, the algorithm then determines the condition of step 335: does a threat with a C threat level exist for the drug. The condition of step 335 is similar to that of step 330 in that the algorithm has already determined whether a C threat level exists for a penetration value of 85. Thus, in the arrangement of algorithm 300, step 335 effectively determines whether a C threat level exists for a penetration value of 0 or greater. If a C threat level exists for a threat associated with the drug, the algorithm assigns a risk rating of blue alert to the pharmaceutical.

If the condition of step 335 is not met, the algorithm 300 then determines the condition of step 340: does a threat with a B threat level exist for the drug. A B threat level indicates a lower degree of risk than a C threat level, which in turn indicates a lower level of risk than a D threat level. If a B threat level exists for the drug, the algorithm assigns a blue risk rating to the drug. If the condition of step 340 is not met, then the drug is assigned a green alert.

It is believed by the inventor that applying the above algorithms to pharmaceuticals and their associated threats will provide users of pharmaceuticals with information that enables them to make more informed decisions about taking their pharmaceutical. In particular, the risk rating resulting from algorithm 300 of FIG. 5 is designed to provide patients the general risk rating and guidance from Table IV. The guidance can be used as an action item that patients can use when taking the pharmaceutical.

TABLE IV

Relationship between Risk Rating, Risk Advisory Conditions and Guidance to Patients

| Risk Rating | Risk Advisory Condition | Guidance to the Patient |
|---|---|---|
| RED | HIGH | Should only be used under strict supervision |
| ORANGE | ELEVATED | Use within a customized risk management plan |
| YELLOW | GUARDED | Be on the lookout for safety events |
| BLUE | GENERAL | Use under the normal care of a physician |
| GREEN | LOW | Suitable for widespread use |

The algorithms described above can be modified to include additional factors. In particular, the algorithms 10 and 300 of FIGS. 1 and 5, respectively, can be modified to include additional factors and variables. For example, the output of the algorithms 10 and/or 300 can be configured to include a step of assessing the strength of the evidence used to support the safety alert. Assessing the strength of the evidence can be based on using the US Preventive Services Task Force (USPSTF) classification. The strength of the evidence can be based, for example, on the following four classifications: (i) evidence obtained from at least one properly designed randomized controlled trial; (ii) evidence obtained from well designed studies; (iii) opinions of respected authorities; and (iv) dramatic implications of this alert, despite lacking evidence. It is intended that other modifications of the algorithms described herein can be made and remain within the scope of the inventions.

The above algorithms are configured to process safety information relating to a drug as applied to a total population of patients administered the pharmaceutical. The algorithms also can be configured to provide safety information for subpopulations based on information provided about sub-populations and individuals. The system can be used to provide personalized risk ratings by recalculating penetration ratings for each threat given the narrower population to which an individual belongs.

For example, a particular anti-hypertensive drug may be taken by both men and women, of all ages, of all races, and in people with and without diabetes. When applying the algorithm 100 to the general population this drug might be assigned a general risk rating of blue. To assign a personalized risk rating to an Asian male with diabetes aged 65 and older, one would re-assign a penetration rating for each individual threat based not on the general population but upon a population of Asian diabetic males aged 65 and older. A particular threat that has a penetration rating of 1 in the general population may have a penetration value of 85 amongst elderly diabetic males. This may result in an increased rating for the product for this narrower population, and a personalized risk rating of orange for the Asian male with diabetes aged 65 and older. As may be evident, only step 115 is not dependent on the definition of the treatment population and the result for the other steps in the algorithm 100 may vary depending upon the definition of the population for whom the risk rating is being determined.

The methods described herein may be implemented in a number of manners. For example, the method of assigning a risk rating may be implemented in software, on a computer system and/or on the Internet. In one implementation, the system implementing the algorithms may be stored and/or run on a central server which gathers, processes, and stores threat information about medical products. In such an implementation, the algorithms described herein may be run on the central server. Alternatively, a user accessing the central server may have software installed on a home computer and the algorithms run on the home computer with data supplied by the central server. Thus, if an individual desires to know more about the safety and risk associated with the pharmaceuticals they may go to the webpage of the system and enter the name of one or more pharmaceuticals. The system then responds back with the risk rating for each pharmaceutical.

The individual may further decide to obtain a more personalized assessment of the risk rating associated with the drug. The individual then would enter information about their demographics (e.g., age, gender, race, weight, etc.) and their health (e.g., hypertensive, elevated cholesterol levels, diabetic, etc.). Depending upon the information already gathered for the drug, the algorithms will be run as described above to assess a more personalized risk rating for the individual.

In one implementation, the webpage and service described above may allow the user to create a private account and specify certain drugs for which they have been prescribed. Each time the user accesses the account, the webpage may display the risk rating for each of the drugs they have selected (e.g., an orange risk rating for one drug, a blue risk rating for another drug, etc.) along with a personalized risk rating for each of the drugs. In this manner, individuals are able to obtain real-time overall and personalized risk ratings for the pharmaceuticals they are being prescribed.

In another implementation, physicians can use a physician-oriented page of the web system to monitor the risk rating of pharmaceuticals they prescribe to their patients along with the personalized risk ratings for each of their patients. The physician-oriented page can be configured to display in one screen all the drugs prescribed by the physician as well as each drug's risk rating. On another screen, the physician can access pharmaceutical information for each patient and view personalized risk ratings. This configuration will allow the physician to notify their patients of potential risk as well as help the physician prescribe pharmaceuticals with more knowledge about the risks and potential threats associated with each drug and each patient.

EXAMPLE

The above methods and systems may be implemented in a webpage as described above. In one example of such a webpage implementation, the user logs onto an account and enters the name for a particular drug. The risk rating displayed on the webpage for the drug will be an indicator of the risk for the drug, e.g., a yellow box adjacent to the drug name. The following example describes one implementation for how a risk rating could be assigned and the box displayed.

Consider a drug, NUSAFEX, used to prevent pregnancy and which has been on the market for nine months. As a result of clinical trials and spontaneous reports, the drug's label identifies the following threats: (1) a generally increased probability of death of approximately 1 in 250,000; (2) a small but notably increased risk of bone fractures in young women; (3) a high risk of death in patients with severe liver damage. Given its branding and the many elements in its label, many patients may be confused about how risky this drug is for them. Applying the algorithms described in the figures above, one would initially evaluate the threat levels using the algorithm of FIG. 4. Applying the algorithm 200 of FIG. 4 to individually rate each of the threats results in threat ratings of A, B, and D, respectively. Applying the algorithm 100 of FIG. 3 to evaluate the penetration rating for each of the individual threats, results in penetration ratings of 85, 15, and 0, respectively. The first threat is general to the entire treatment population, which is greater than 85% of the treatment population and therefore is assigned a penetration rating of 85. The second threat is specific to young women that make up more than 15% of the treatment population (i.e., women taking contraceptives) and therefore a penetration rating of 15 is assigned. The third threat is specific to people with severe liver damage that make up much less than 1% of the treatment population and therefore is assigned a penetration rating of 0. This results in individual threat ratings of A85, B15, and D0.

Applying the algorithm 300 of FIG. 5, the algorithm will find a match at step 325 because NUSAFEX has been on the market for less than two years and will result in a risk rating of yellow. This allows a young woman considering contraceptive options to balance the newer benefits of NUSAFEX against its yellow risk rating to make a more informed decision about taking NUSAFEX instead of an older contraceptive that lacks the new benefits but has a blue rating. In the absence of the methods described herein, the woman would not have the ability to make as informed a decision without research.

As another example of how the algorithms described herein can be used to generate a personalized risk rating, one could imagine a nineteen year old female with chronic hepatitis and significant liver dysfunction. Although the threat levels remain A, B, and D, the penetration ratings for each individual threat in this narrower treatment population of patients with chronic hepatitis will now be 85.15, 85 since the third threat will apply to more than 85% of patients in this treatment population. In applying algorithm 300, the resulting risk rating for 19 year women with chronic hepatitis and significant liver dysfunction will be red because the newly calculated D85 will match at step 305. The 19 year old woman is able to easily comprehend the risk associated with NUSAFEX without needing to look into details.

While several particular forms of the invention have been illustrated and described, it will be apparent that various modifications and combinations of the invention detailed in the text and figures can be made without departing from the spirit and scope of the invention. For example, references to utilities or applications are also not intended to be limiting in any manner. Similarly, references to specific indicators, colors, symbols, letters, numbers and the like are exemplary only and may be varied within the scope of the inventions. Accordingly, it is not intended that the invention be limited, except as by the appended claims.

What is claimed is:

1. A method implemented on a computer system for assigning a risk rating to a medical product, the method comprising:
using the computer system programmed with an algorithm for assessing one or more threats associated with the medical product, wherein assessing one or more threats associated with the medical product includes determining a probability of the threat occurring, and using the value of the probability of the threat occurring to determine and assign a threat value to the threat and storing the threat value on a readable medium, and wherein determining the probability of one or more threats occurring comprises pooling the probability of multiple threats occurring to give a pooled probability and assigning a single probability value for the pooled probability of the multiple threats;
using the computer system programmed with an algorithm for assessing the level of experience with the medical product, wherein assessing the level of experience with the medical product includes assessing the level of experience with the medical product based on a level of usage of the product, assigning an experience value to the level of experience, and storing the experience value on a readable medium, wherein the level of usage of the medical product comprises years on the market, number of prescriptions, number of patients studied during the clinical trials, number of patients taking the product, and number of countries in which the product has been approved and marketed; and using the computer system programmed with an algorithm for assigning a risk rating for the medical product to provide an indication of risk associated with the medical product, wherein the risk rating for the medical product is assigned based on the threat value and experience value and the computer system is programmed to display the resulting risk rating on a display.

2. The method of claim 1, wherein assigning a risk rating to the medical product comprises using the risk rating algorithm programmed on the computer system to assign a risk rating to one or more of a pharmaceutical product, a biologic product, and a medical device.

3. The method of claim 1, wherein assessing one or more threats further comprises assessing the severity of the threat.

4. The method of claim 3, wherein assessing the severity of the threat comprises assessing one or more of a risk of permanent disability, death, and serious adverse event.

5. The method of claim 1, wherein assessing one or more threats further comprises assessing the potential population affected by the threat.

6. The method of claim 5, wherein assessing the potential population affected by the threat further comprises assessing a percentage of the population to which the threat applies.

7. The method of claim 5, wherein assessing the one or more threats further comprises one or more of determining the population to which the threat applies, determining whether the population at risk as a result of the threat can be identified in advance, and determining an indicator of usage of a second medical product for which there is an interaction with the first medical product.

8. The method of claim 1, further comprising pooling the assessment of each threat.

9. The method of claim 1, further comprising determining whether the medical product is an orphan product.

10. The method of claim 1, wherein assigning the risk rating comprises assigning a gradated rating having at least three grades.

11. The method of claim 10, wherein assigning the three grades comprises assigning a gradated rating having three symbols.

12. The method of claim 1, wherein the method uses the algorithm for assessing one or more threats programmed on the computer system to assess more than one threat.

13. The method of claim 1, wherein assigning a risk rating further comprises using software programmed on the computer system to provide and display guidance associated with the risk rating.

14. The method of claim 1, wherein the method for assigning a risk rating to a medical product is implemented on a webpage.

15. A webpage for providing a risk rating for a medical product, the webpage configured to:
receive input relating to a medical product; and
display a risk rating for the medical product;
the webpage including software instructions programmed on a computer system for processing the input relating to the medical product to retrieve data relating to an assessment of one or more threats associated with the medical product wherein assessing one or more threats comprising determining a probability of the threat occurring, retrieve data relating to an assessment of the level of experience with the medical product based on a level of usage of the product, wherein the level of usage of the medical product comprises years on the market, number of prescriptions, number of patients studied during the clinical trials, number of patients taking the product, and number of countries in which the product has been approved and marketed, and assign a risk rating for the medical product to provide an indication of risk associated with the medical product, the risk rating being based on the threats associated with the medical product and the level of experience with the medical product, wherein determining the probability of one or more threats comprises an assessment of the probability of multiple threat occurring to give a pooled probability.

16. The webpage of claim 15, wherein the medical product comprises one or more of a pharmaceutical product, a biologic product, and a medical device.

17. The webpage of claim 15, wherein the assessment of one or more threats further comprises an assessment of the severity of the threat.

18. The webpage of claim 17, wherein the assessment of the severity of the threat comprises an assessment of one or more of a risk of permanent disability, death, and serious adverse event.

19. The webpage of claim 15, wherein the assessment of one or more threats further comprises an assessment of the potential population affected by the threat.

20. The webpage of claim 15, wherein the risk rating comprises at least three grades.

21. The webpage of claim 20, wherein the three grades comprise three symbols.

22. The webpage of claim 15, wherein the webpage is programmed with software instructions for retrieving data relating to an assessment of more than one threat.

23. The webpage of claim 15, wherein assigning a risk rating further comprises providing guidance associated with the risk rating.

24. The webpage of claim 19, wherein assessing the potential population affected by the threat further comprises assessing a percentage of the population to which the threat applies.

25. The webpage of claim 15, wherein assessing the one or more threats further comprises one or more of determining the population to which the threat applies, determining whether the population at risk as a result of the threat can be identified in advance, and determining an indicator of usage of a second medical product for which there is an interaction with the first medical product.

26. The webpage of claim 15, further comprising determining whether the medical product is an orphan product.

27. The webpage of claim 15, wherein the webpage is displayed on a screen.

* * * * *